United States Patent [19]

McGuire

[11] 4,236,402
[45] Dec. 2, 1980

[54] METHOD AND APPARATUS FOR TESTING ROCK TENACITY

[75] Inventor: Robert C. McGuire, Dublin, Ohio

[73] Assignee: Dresser Industries, Inc., Dallas, Tex.

[21] Appl. No.: 31,575

[22] Filed: Apr. 19, 1979

[51] Int. Cl.³ .......................... G01N 3/30; G01N 3/48
[52] U.S. Cl. ........................................... 73/12; 73/82; 73/425.2
[58] Field of Search ............... 73/12, 82, 421 R, 425.2

[56] References Cited

U.S. PATENT DOCUMENTS

| 2,216,989 | 10/1940 | St Clair | 73/421 |
| 3,732,725 | 5/1973 | Allen et al. | 73/81 |

FOREIGN PATENT DOCUMENTS

565226  7/1977  U.S.S.R. .................... 73/425.2

*Primary Examiner*—S. Clement Swisher
*Attorney, Agent, or Firm*—John M. Lorenzen; Paul E. Krieger

[57] ABSTRACT

A method for performing strength tests on material to be mined includes the steps of preparing a flat surface on the material to be tested, forming one or more grooves in the flat surface, impacting the flat surface with a test device at a predetermined angle and at a predetermined force which is at least as great as that necessary to break out material located between the impact point and groove, repeating the preceding step at a predetermined distance from the first impact, at substantially the same force and at substantially the same angle.

An impact guide and sample collector guides the test device toward the test surface at a predetermined angle and collects material broken out during the test.

19 Claims, 5 Drawing Figures

METHOD AND APPARATUS FOR TESTING ROCK TENACITY

BACKGROUND OF THE INVENTION

This invention relates to a method and apparatus for testing the strength of rocks and, more particularly, to simulate the action of cutting bits of a mining machine for developing design criteria.

Many tests have been developed for determining the hardness and other characteristics of rock. Devices such as the one shown in U.S. Pat. No. 3,732,725, where an impact gun is used, have been developed for testing compressive strength of materials. Other devices, such as the one shown in U.S. Pat. No. 3,618,369, where a rock specimen is stressed until deformation occurs, have been used to measure the amount of permanent deformation along with the static force necessary to effect the deformation for developing a "penetration index" to use in conjunction with rotary rock cutters on a tunneling machine. Other types of devices are shown in U.S. Pat. Nos. 2,620,386 and 3,056,952, where the hardness of earth strata is tested in conjunction with mining machines.

However, there is no known method or device which has been developed which simulates the action of the cutting bits of a mining machine to determine optimum spacing between adjacent bits, the most efficient sequence in which multiple bits should strike the surface to be mined, the preferred angle of attack and optimum torque of the cutting head. These characteristics should be known so that a continuous mining machine can be designed for maximum performance.

SUMMARY OF THE INVENTION

In accordance with the invention, a method and apparatus have been developed which simulate bit action in both cleated material such as coal where planes of sedimentation are present which dictate breakage characteristics along predictable angles and relatively homogeneous material such as phosphate where rock is not broken along definite planes.

Because of the difficulty of determining the exact orientation of material to be mined, especially coal, the mine face itself is tested. The face is prepared by forming a flat surface with a disc grinding device. A horizontal groove is cut in the surface. A test device in the form of a carbide tip propelled from a gun, such as one used for spear fishing where gas under pressure is used as a propelling medium, is used for impacting the flat surface at a point spaced apart from but in close proximity to the groove. The carbide tip is propelled at a predetermined angle toward the groove, that angle simulating the angle of attack of the carbide tips of a continuous mining machine when it is sumped straight into the mine face. For convenience purposes during testing, the tip is propelled upwardly which would simulate the complement to the angle of the continuous miner bits which rotate clockwise and downwardly during mining operations.

The bit is propelled into the face at a force which is at least as great as that necessary to overcome the threshold strength of the material so that material located between the impact point and groove will be broken out of the face.

The tip is guided by a combination guide and sample collector where the broken out material can be collected for later volumetric and particle size analysis. A second impact is performed at a predetermined distance from the first point at substantially the same force, angle and distance from the groove. Additional impacts are performed until an optimum distance between impacts is determined by observing when material broken out from between adjacent impact points equals the distance between the impact points with minimal overlapping. This method has been found suitable for cleated material such as coal where the orientation of the cleavage angles is significant in determining optimum cutting characteristics.

For relatively homogeneous materials, such as phosphate, where defined cleavage planes are not a significant factor, a similar but slightly different method can be used. In this method a flat surface is also prepared, but a pair of grooves are formed perpendicular to each other in the flat surface. A carbide tip is used to impact the flat surface at an angle normal to the surface and along a line bisecting the angle formed by the grooves at a point far enough away from the intersection of the grooves so that material located between the impact point and groove intersection will not break out from the face. Another impact is performed along the bisection line closer to the intersection until a point farthest from the intersection is determined where material located between the impact point and the groove intersection will be broken out. In this way, a point is determined where the threshold strength of the material is overcome at a predetermined force.

The combination impact guide and sample collector includes a housing which covers the portion of the mine face where material will be broken out and includes a guide opening extending through the housing at a predetermined angle to the face. The housing also includes an opening in its bottom portion around which a sample collecting bag can be held for collecting material which has been broken out for later analysis.

BRIEF DESCRIPTION OF THE DRAWINGS

A better understanding of the invention can be obtained from a detailed description of preferred embodiments set forth below when taken in conjunction with the accompanying drawings in which.

DETAILED DESCRIPTION OF PREFERRED EMBODIMENTS

Figure 1:
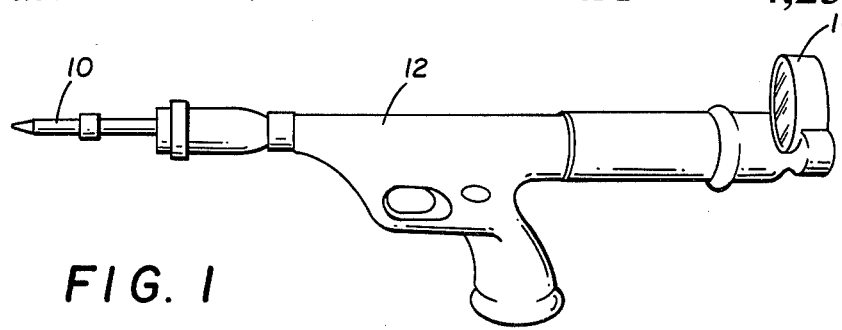
FIG. 1 is a perspective view of a test device formed with a carbide tip and a gun which can be used to propel the test device.

In order to conduct a strength test in accordance with the subject invention, a replaceable carbide tip test device 10 as shown in FIG. 1 is used which simulates the action of cutting bits used on a continuous mining machine (not shown). This invention is not restricted to use of carbide tips, but other appropriate devices for simulating other types of mining or cutting apparatuses could also be used in accordance with the invention. As shown in FIG. 1, the carbide tip 10 is adapted to be propelled by a standard spear fishing gun 12 which utilizes gas under pressure for propelling the tip 10. A detailed description of the gun 12 will be omitted since it is a standard item. For tests described below nitrogen gas under pressure of 400 p.s.i. was used as indicated on a pressure gauge 14 mounted at the rear of the gun 12. Alternate tips with varying cone angles may be used to simulate actual cone angles of commercially available bits.

The invention is not restricted to the use of the gun 12 and other types of propelling means could also be used, especially under conditions where pressurized gas containers are not permitted. For example, spring loaded percussive devices or devices allowing hand delivered impact of a guided actual bit of the various designs commercially available could be used where the propelling force can be determined and controlled.

The primary purpose of the test device 10 is to simulate the action of the cutting bits of a continuous mining machine so that the spacing of the bits on the cutting head as well as other design criteria can more accurately be determined for optimum performance. In order to provide meaningful data, especially for cleated material such as coal, tests should be conducted in situ so that data will be generated from the orientation of cleavage surfaces identical to those which would be encountered during mining operations. Therefore, a mine face should be prepared by grinding a flat surface on the face generally perpendicular to the mine roof and floor. This can be done by utilizing a standard disc grinding machine (not shown) adapted for this specific purpose.

Figure 2:
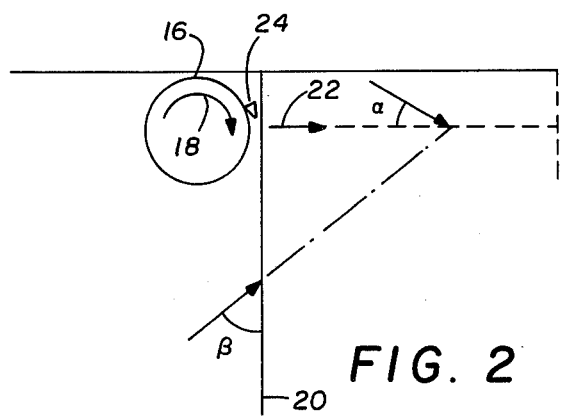
FIG. 2 is a schematic view of the action of the cutting head of a continuous mining machine.

In order to facilitate a better understanding of the invention, the action of a cutting head is shown in FIG. 2 where the cutting head is shown schematically and designated by reference number 16. As shown by arrow 18, the head 16 rotates in a clockwise direction. As the head 16 advances or is "sumped" toward a face 20 of a coal seam in the direction shown by arrow 22, cutting bits designated by reference numeral 24 will engage the coal at an angle $\alpha$ which, for illustrative purposes, is 45°. In order to simulate the cutting action of the bits 24, the complement to $\alpha$ represented by the angle $\beta$ will be utilized by the test device as described in detail below.

Figure 3:
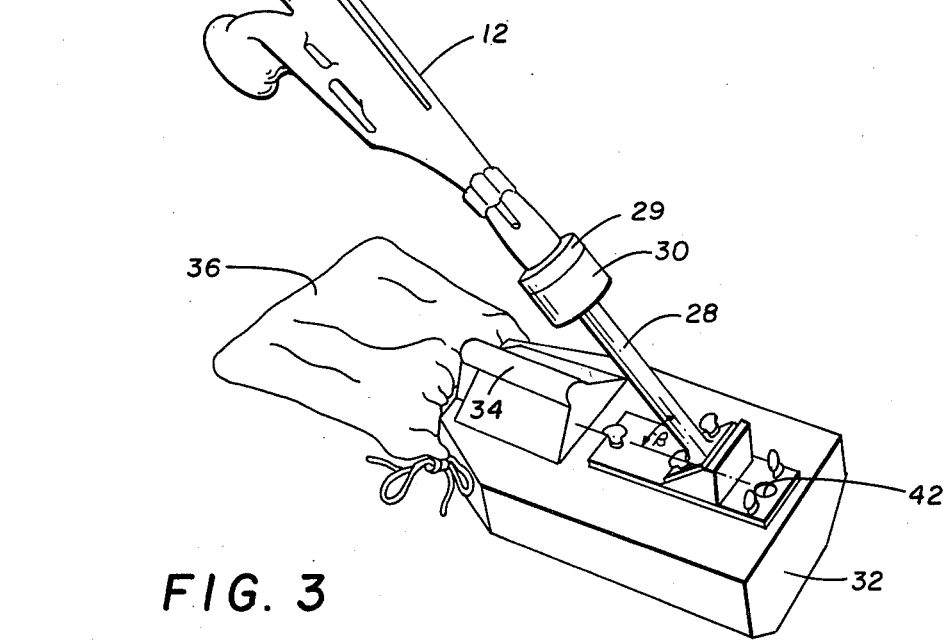
FIG. 3 is a perspective view of a combination test device guide and sample collector for guiding the carbide tip at a predetermined angle relative to a mine face and collecting broken out material.

In order to insure that the bit 10 is impacted on the mine face 20 at a constant angle for each impact and that broken away coal or other rock does not strike the operator and can be collected for subsequent analysis, a combination guide and sample collector shown in FIG. 3 has been developed as part of the invention. The device is designated generally by reference numeral 26 and includes a hollow bit guide 28 which is oriented at a predetermined angle $\beta$. As shown in FIG. 3, a stop 29 on the gun 12 engages a mouthpiece portion 30 of the guide 28 so the bit 10 is positioned at a predetermined set distance away from the mine face 20, in the case of the tests which will be described below that distance being 10 inches. The remainder of the device 26 is in the form of a housing 32 which includes a handle 34 for holding the device 26 in place during operation. A sample collecting bag 36 can be attached around a collar (not shown) or the like at the bottom of the housing 32 for collecting coal or other rock broken away from the mine face 20 during the test.

Figure 4:
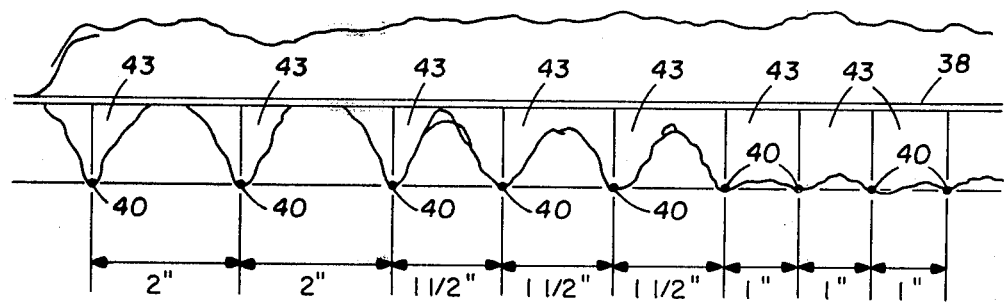
FIG. 4 is a pictorial sketch of the results of impacting a coal mine face with a carbide bit at spaced-apart intervals.

In order accurately to simulate the action of the bit 24, a groove 38 as shown in FIG. 4 is cut into the prepared portion of the mine face 20, the groove 38 being horizontal and normal to the mine face. For the test described in detail below the groove 38 is about 1½ inch deep and 3/16 inch wide. The groove can be cut by using a rotary cutting wheel (not shown) adapted especially for this use.

As shown in FIG. 4, the mine face 20 is impacted at a number of points 40 spaced apart from each other along a line 41 parallel to the groove 38. In operation, a series of points 40 are indicated on the prepared portion of the mine face 20 parallel to the groove 38, the points being spaced apart at different distances to determine optimum spacing of adjacent cutter bits. After the points are determined, the test bit 10 is inserted into the guide 28 of the guiding and collecting device 26 which is then placed over the mine face, the point of impact being observable through an opening 42 located in the device 26 or controllable by aligning the edge of the collecting device 26 in a predetermined fashion. The bit is propelled by the gun 12 and then the process is repeated for each of the points 40 as shown in FIG. 4.

An example of the method is shown in FIG. 4 where broken out portions of coal 43 are indicated between the impact points 40 and the groove 38, the broken out portions 42 between the points which are spaced 2 inches from each other not totaling the entire distance between the points 40 which indicates that those points were too far apart. For the points 40 which are 1 inch apart, too much coal was broken out which indicates that the points are too close together. However, for the points which are 1½ inches apart, optimum break out amounts are shown where there is a slight overlap between the broken out portions for adjacent points 40 which indicates that the cutter bits will operate at or close to maximum efficiency. For the test results shown in FIG. 4, the impact points 40 are located 1 inch from the groove 38 and the bit 10 was propelled at an angle $\beta$ of 45°. The propelling force is not considered to be critical except that it should be at least as great as that necessary to break out material located between the impact 40 and the groove 38. When nitrogen gas under 400 p.s.i. is utilized in the gun 12, satisfactory results are obtained for coal.

The test just described is deemed appropriate for material such as coal where there are definite cleavage planes along which coal normally breaks so that in situ testing is appropriate for determining the best cutting characteristics. As part of the determination, the total volume of broken material can be gathered for volumetric and particle size analysis for each impact.

Figure 5:
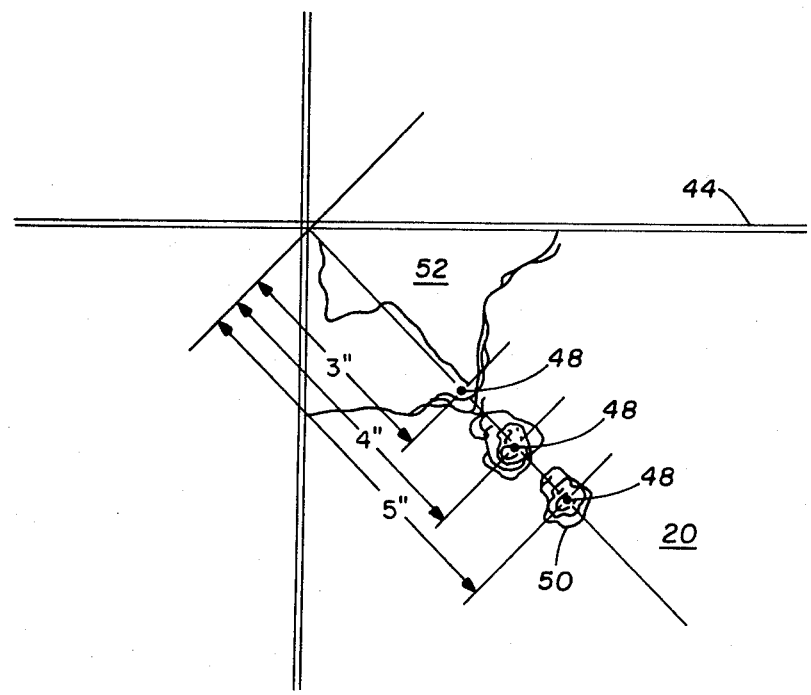
FIG. 5 is a pictorial sketch of the results when the test device is used for impacting relatively homogeneous material.

For relatively homogeneous materials such as potash, a similar test can be conducted to determine the tenacity or when the threshold break out strength is overcome for that type of material at a predetermined force. The same testing device as shown in FIG. 1 as well as propelling gun can be used in a way as shown in FIG. 5. For this type of test, the tip 10 can be propelled normal to the mine face or other test surface which is prepared in a manner similar to that described for the test shown in FIG. 4. One difference is that two grooves 44 and 46 are formed in the prepared surface which are perpendicular to each other. These grooves can be about 3/16 inch thick and about 1½ inch deep. In order to determine the threshold break out strength of the material being tested, impact points 48 are determined along a line which bisects the intersection of the grooves 44 and 46 as shown in FIG. 5. A guiding and collecting device similar to that of FIG. 3 but adapted to guide the carbide tip 10 at an angle normal to the mine surface 20 can be used for guiding the tip 10 toward the impact points 48. The point 48 farthest from the intersection of the grooves 44 and 46 is first impacted, this point being far enough away from the intersection that material located between the impact point 48 and the groove intersection will not break out from the mine surface 20 as shown by the impact area 50. This process is repeated at spaced intervals of about ½ inch moving toward the intersection of the grooves 44 and 46 until a point is reached where material located between the impact point 48 and groove intersection will break out as shown by the break out portion designated by reference number 52.

This distance represents the point at which the threshold strength of the rock is overcome by a predetermined force (which can be translated into cutter head torque) for determining cutting head penetration rate in inches per revolution which equals cutting head speed in R.P.M.'s divided by sump advance rate at unit distance per minute.

In this way, the action of a continuous miner is simulated so that optimum bit spacing and other parameters can be determined without reverting to full scale trial-and-error techniques necessary in the past. Maximum performance can now be predicted prior to manufacturing a mining machine and actually operating it in a mine. It should be understood that the embodiments of the invention shown and described above can be modified and improved by those skilled in the art and that all such modifications and improvements are contemplated as falling within the scope of the appended claims.

The embodiments of the invention in which an exclusive property or privilege is claimed are defined as follows:

1. Method for performing strength tests on material to be mined, comprising the steps of:
   (a) preparing a flat surface on the material to be tested,
   (b) forming a groove in the flat surface,
   (c) impacting the flat surface with a test device spaced apart from but in close proximity to the groove at a predetermined angle toward the groove and at a predetermined force which is at least as great as that necessary to break out material located between the impact point and groove,
   (d) repeating step (c) at a predetermined distance from the first impact, at substantially the same force and at substantially the same angle and distance from the groove,
   (e) repeating steps (c) and (d), if necessary, until optimum spacing is determined by observing the amount of material broken out between adjacent impact points.

2. The method of claim 1, wherein the flat surface of step (a) is substantially vertical.

3. The method of claim 1, wherein step (b) includes forming the groove perpendicular to the flat surface.

4. The method of claim 3, wherein the groove is about 1½ inch deep and 3/16 inch wide.

5. The method of claim 1, wherein step (c) includes impacting the flat surface with a carbide tip.

6. The method of claim 1, wherein the predetermined angle of step (c) is about 45°.

7. The method of claim 1, wherein the test device is held about 10 inches from the flat surface and is propelled by a gun utilizing compressed gas as a propelling means.

8. The method of claim 1, wherein the predetermined distance of step (d) is about 2 inches and steps (c) and (d) are repeated by decreasing the predetermined distance by ½ inch for each repeat.

9. Method for performing strength tests on material to be mined, comprising the steps of:
   (a) preparing a flat surface on the material to be mined,
   (b) forming grooves intersecting and perpendicular to each other in the flat surface,
   (c) impacting the flat surface with a test device normal to the surface and along a line bisecting the angle formed by the grooves, at a predetermined force which is at least as great as that necessary to break out material located adjacent to the grooves, but far enough away from the intersection so that material located between the impact and groove intersection will not break out from the flat surface,
   (d) repeating step (c) at a predetermined distance from the first impact but closer to the intersection and at substantially the same force until a location farthest from the intersection is determined where material located between the impact and groove intersection will break out from the flat surface.

10. The method of claim 9, wherein the flat surface of step (a) is substantially vertical.

11. The method of claim 9, wherein the grooves of step (b) are substantially perpendicular to the flat surface.

12. The method of claim 11, wherein the grooves are about 1½ inch deep and 3/16 inch wide.

13. The method of claim 9, wherein step (c) includes impacting the flat surface with a carbide tip.

14. The method of claim 9, wherein the test device is held about 10 inches from the flat surface and is propelled by a gun utilizing compressed gas as a propellent.

15. The method of claim 9, wherein the predetermined distance of step (d) is about ½ inch.

16. Impact guide and sample collector for conducting tests on substantially vertical surfaces, comprising a housing with outer and inner sides, the inner side including a collecting compartment adapted to be held against the vertical surface for catching material falling therefrom, guide means including an opening extending through the housing for guiding an impact device at a 45° angle toward the surface, and means for holding the housing in place relative to the surface while the impact device is propelled through said opening.

17. A combination guide and fragment collector for use with an impact projectile propelling device in conducting rock strength tests on a substantially vertical surface, such as a mine face, comprising:
   a housing with inner and outer sides, the inner side being adapted to fit against the vertical surface and including a collecting cavity adapted to surround a pre-selected impact point;
   guide means including an opening extending through the housing, one end of the guide being adapted to mate with the discharge outlet of a projectile propelling device and to receive a propelled impact projectile and guide the projectile toward the pre-selected impact point;
   a fragment collecting compartment connected to the cavity in the housing for receiving rock fragments broken from the surface by the impact of the projectile; and means on the outer side of the housing separate from the guide means for holding the guide and fragment collector in place against the surface while the impact projectile is propelled therethrough.

18. A combination guide and fragment collector as recited in claim 17, wherein the means for holding it against the rock surface consists of a handle on the outer side of the housing.

19. A combination guide and fragment collector as recited in claim 17, further including a second opening in the housing through which the operator can observe the selected impact point in order to align the guide.

* * * * *